United States Patent [19]

Devers

[11] 4,192,300
[45] Mar. 11, 1980

[54] BANDAGE WITH INTEGRATED APPLICATOR

[76] Inventor: John C. Devers, 7004 Armat Dr., Bethesda, Md. 20034

[21] Appl. No.: 913,121

[22] Filed: Jun. 6, 1978

[51] Int. Cl.² .............................................. A61L 15/00
[52] U.S. Cl. .................................... 128/155; 128/260; 128/268
[58] Field of Search ............... 128/155, 156, 169, 170, 128/171, 260, 268, 269

[56] References Cited

U.S. PATENT DOCUMENTS

| | | | |
|---|---|---|---|
| 2,280,506 | 4/1941 | Betts | 128/156 |
| 2,785,677 | 3/1957 | Stumpf | 128/156 |
| 3,521,631 | 7/1970 | Gardner et al. | 128/156 |
| 4,005,709 | 2/1977 | Laerdal | 128/155 |

*Primary Examiner*—John D. Yasko
*Attorney, Agent, or Firm*—James J. Brown

[57] ABSTRACT

The invention concerns a bandage having an applicator attached to the backing of the bandage and disposed to extend vertically from the top surface of the bandage to permit pressure to be applied downward against the backing or the centrally disposed absorbent pad of the bandage. Advantageously, a swab of impregnated absorbent material in a package is attached to the remote end of the applicator. The applicator can be one or more rigid strips of material attached to the bandage backing or a rigid, hollow tube dispose vertically over the central portion of the bandage.

14 Claims, 11 Drawing Figures

BANDAGE WITH INTEGRATED APPLICATOR

The present invention is directed to a unitary bandage having an integrated applicator which facilitates application of the bandage without contacting or contaminating the sterile or medicated portion of the bandage. In one further embodiment of the present invention both the bandage and applicator can be fabricated in a single piece thereby reducing cost. In yet a further embodiment of the present invention, the applicator may be provided with a sealed swab impregnated with antiseptic or cleansing material as an integral part of the bandage, thereby facilitating availability and dispensing of the material in a sanitary manner.

BACKGROUND OF THE INVENTION

Bandages which have heretofore been known in the art and which have found wide spread use both in the home and hospitals have generally consisted of a flexible piece of backing material having adhesive on one or more portions of one side and a centrally disposed absorbent portion. Usually the sterile absorbent material as well as the adhesive surfaces are protected from contamination and sticking by the provisions of one or more pieces of protective film which are peeled away from the adhesive and absorbent surface before applying the bandage. Such bandages are usually also packaged in small envelope like containers which are opened by tearing.

Although such bandages are relatively inexpensive and have been widely used, they suffer from a number of disadvantages. In most instances both hands must be employed to open the envelope containing the bandage and remove the protective film from the adhesive and sterile surface of the bandage prior to application. Further, in most instances the portion of the protective film which is grasped in order to remove it from the adhesive surface is the portion directly opposed to the sterile surface. Thus, the fingers of the person applying the bandage of necessity come into close proximity with the sterile portion of the bandage greatly increasing the risk of contamination. Once the protective film is removed from such conventional bandages and they are ready to apply, the additional problem is presented of properly holding the bandage while it is placed on the skin in the desired location. In general, such applications require both hands and are inconvenient at best.

Still a further disadvantage in operations in which conventional bandages are employed for certain types of therapy is that applications of antiseptic or other medicinal preparations must be made separately such as by the use of cotton or other absorbent swabs which are not always immediately available. For example, in the common procedure of drawing blood from an individual, it is first necessary to separately employ a cotton swab impregnated with alcohol or other fluid to cleanse the area where the needle will be inserted and then separately to open and apply a bandage of the type described above. Such procedures are not only cumbersome and time consuming, but involve the additional risk of contamination through contact with the fingers.

Finally, because of the separate packaging and manner in which the protective coverings are employed in conventional bandages, a number of fabrication procedures are actually involved which contribute to the expense of such bandages.

Accordingly, it is an object of the present invention to provide an integrated, self contained bandage which is both easier and more efficient to open and apply than bandages of the type described above.

It is still a further object of the present invention to provide an improved self contained bandage which permits sterility to be better maintained by avoiding the likelihood of contact with the sterile area of the bandage prior to application.

It is still a further object of the present invention to provide a bandage which can be fabricated in one piece.

It is still a further object of the present invention to provide a bandage in which an applicator for antiseptic or other medicinal preparation can be integrated with the bandage to facilitate its use and availability.

STATEMENT OF THE INVENTION

These and other objects are achieved according to the present invention wherein a unitary bandage is provided having an integrated applicator for applying the bandages without contacting the sterile or medicated portion of the bandage. In essence, the self contained bandage of the present invention comprises an absorbent pad a portion of which projects through a flexible or semi-rigid backing to the other side and an applicator for applying the bandage which may be integrated with a top covering for covering the top of the pad and backing. The top cover is generally coextensive with and adapted to lay flat against the top of the absorbent pad and backing and is removably attached to the backing either at the end of the bandage or one side. A bottom cover is provided for covering and enclosing the antiseptic surface of the absorbent pad and may also cover the underside and edges of the backing. The bottom cover may be flexibly and removably attached to the backing either at one end or along one of the sides.

As will be apparent from a more detailed consideration of the figures described hereinafter, several embodiments of the present invention are contemplated.

Particularly for applications in which cleansing of the skin or the application of medication such as antibiotics is contemplated, it is desirable that the bandage of the present invention be provided with a swab of absorbent material which is impregnated with the antiseptic or medicinal material such as alcohol iodoform or an antibiotic. Such an impregnated swab can advantageously be attached at one end of the applicator in a small sealed packet.

The applicator used for applying the bandage of the invention is made of rigid or semi-rigid material and is removably disposed on the top side of the backing material so that it extends in a generally vertical direction from the backing and provides both a convenient handle for holding the bandage prior to application and a means for applying downward pressure on the bandage while it is being applied.

In one embodiment of the invention the applicator is a single strip of material which is flexibly and removably attached at one of its ends to a side of the backing and can lay substantially flat over the backing and absorbent pad to form a protective cover. The strip is further provided with a flexible portion, preferably near the point of attachment to the backing, so that it can readily be turned upward to a position vertical to the backing.

In a further embodiment of the invention the applicator is formed by a pair of strips which are each flexibly and removably mounted at opposing edges of the backing and centrally joined over the absorbent pad to extend upward to form a single strip.

In still a further embodiment of the invention, the applicator is a rigid, hollow tube which is disposed vertically to the backing of the bandage and actually encloses the absorbent pad and forms a protective cover as well as an applicator.

Although the top of the bandage, i.e. the non-adhesive coated side, can be protected, in the manner described above, by the applicator in its various embodiments, a separate top protective cover can also be employed. Such a top cover is made of rigid or semi-rigid material and is flexibly attached advantageously at one end or side to an edge of the backing opposite the side to which the bottom cover is attached.

The bottom cover of the bandage of the present invention is also conveniently made of a rigid or semi-rigid material and flexibly and removably attached to one end of the backing. The bottom cover may be contoured or provided with upturned edges so that when it is placed flat against the underside of the backing it also encloses the sides of the backing and the top cover and applicator of the bandage to provide a compact, well sealed unit.

Prior to use, the bottom cover of the bandage, which is flexibly and removably attached such as by providing a weakened, perforated attachment to the backing, is folded away from the surface of the bandage to expose the adhesive coated underside of the backing material. The bandage is then conveniently applied and the bottom covering removed after the bandage is in place by simply tearing away from the ends of the backing.

A particularly advantageous embodiment of the present invention is provided by employing a pressure bandage of the type described in my co-pending application Ser. No. 850,010 in which means are provided for depressing the pad of absorbent material against the immediate area of application and retaining the depressed configuration so that pressure is maintained in this localized area. Such pressure retaining means are conveniently provided by a raised cap portion provided in the top cover of the bandage. Alternatively, where conventional absorbent material forming a bulge in the underside of the bandage is employed a similar protective cap can be provided in the underside of the bottom cover to accommodate the absorbent material.

DETAILED DESCRIPTION OF THE INVENTION

Figure 1:
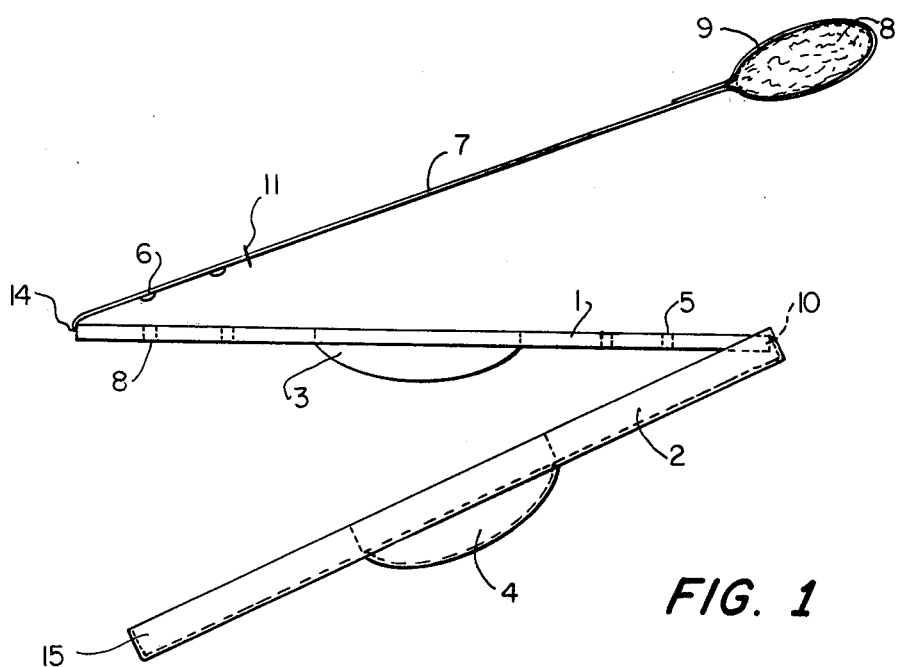
FIG. 1 is a side view of the integrated bandage of the present invention including an applicator employing a conventional absorbent pad and provided with an enclosed swab attached to the end of the applicator.
Figure 2:
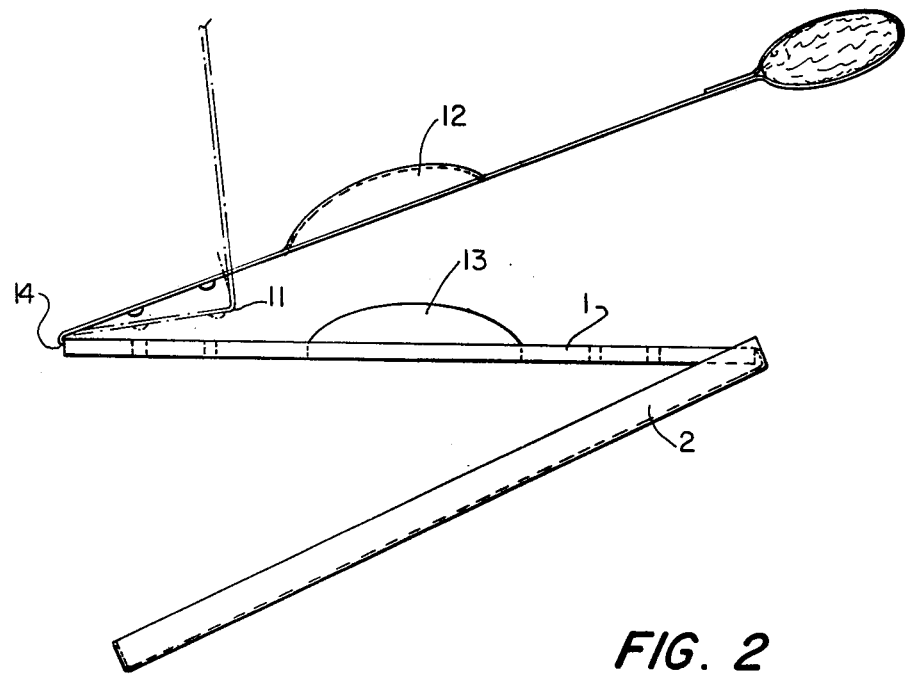
FIG. 2 is also a side view of the present invention employing a pad of absorbent material adapted to maintain pressure in a localized area. The figure further shows in phantom the manner in which the top cover of the bandage is bent at right angles to serve as an applicator.
Figure 3:
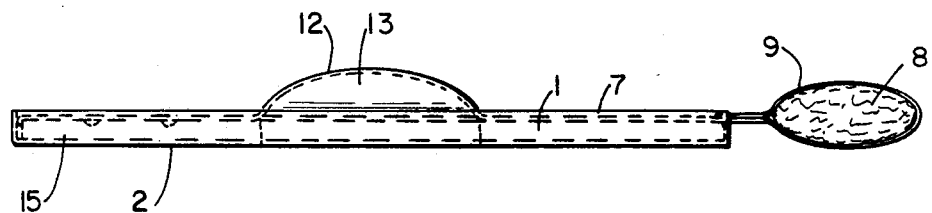
FIG. 3 shows the embodiment of FIG. 2 in which both the top and bottom covers are compressed together to form generally flat packaged bandage.

Directing attention to FIG. 1, a layer of backing material 1 is shown which may be semirigid or flexible. Flexibly attached at one end to this layer of backing material is the protective cover 2 for the bottom side of the bandage which is roughly tray like in form having side and end walls 15 of sufficient height to enclose the other portions of the bandage when they are collapsed and flattened as shown in FIG. 3. Although not shown, it will be understood that the underside of the backing 1 is provided with adhesive material on either side of or around the absorbent pad 3 which can be cotton or gauze, for example, and which will usually be centrally disposed on the backing. In its conventional configuration, the absorbent pad 3 forms a bulge in the bottom of the bandage and is accommodated by an indented portion 4 in the bottom protective layer 2. Flexibly attached to the backing 1 at 14 is the applicator 7, which is also a top protective cover. This attachment at 14 is the applicator 7, which is also a top protective cover. This attachment at 14 is both flexible to permit the applicator 7 to be raised and weakened such as by perforations so that it can easily be torn away from the backing 1. As previously noted, the cover 2 is similarly attached at 10 to the backing material. A flexible area 11 is also provided on the applicator 7 at a short distance from the point of attachment of the applicator to the backing in order to permit it to be bent upward, as shown in FIG. 2, so that it provides a convenient handle for applying the bandage. Air holes 5 are provided in the backing material 1 in the area covered on the underside by adhesive. A portion of these air holes are also adapted to receive and hold the projections 6 in the end of the applicator 7 attached to the backing material 1. This is done so that the end portion of the applicator remains in place against the backing 1 when the rest of the applicator 7 is bent upward.

Conveniently a swab of absorbent material 8 which may be impregnated with antiseptic solution such as alcohol is provided at the tip of applicator 7 remote from the point of attachment to the backing. This swab is conveniently enclosed by a sealed package such as foil or plastic 9 which can easily be ruptured to expose the impregnated swab of material prior to use.

In FIG. 2 the downwardly disposed pad of absorbent material described in FIG. 1 is replaced by a pad of absorbent material 13 which can be downwardly displaced beyond the bottom surface of the backing 1 to form a bulge and pressure maintained in that position by means of a deformable disc or bubble of material 12 which is disposed in the applicator 7 to enclose the pad of material 13. This device is described in more detail in my co-pending application Ser. No. 850,010, filed Nov. 9, 1977. In this embodiment the disc or bubble 12 is formed of a collapsible material to which pressure can be applied to the absorbent pad 13. The bubble 12, however, once it is collapsed has sufficient rigidity to retain its collapsed configuration thereby applying a persistent pressure retaining force against the top of the absorbent pad 13, which force is exerted to cause the absorbent material to remain in pressurized contact with the undersurface of the skin directly opposed thereto.

Figure 4:
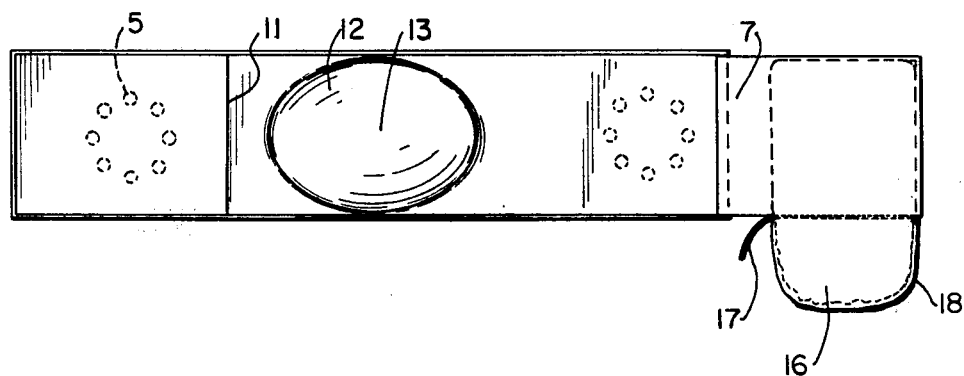
FIG. 4 is a top view of the bandage of the present invention showing an enclosed swab mounted to the side of one end of the applicator of the bandage.

In FIG. 4 of the drawing the swab of absorbent material 16 is shown mounted to the side of one end of the applicator 7 and enclosed in a removable sealed packet 18. Opening of the sealed packet 18 is conveniently accomplished by means of a string or tear flap 17.

Figures 5, 6:
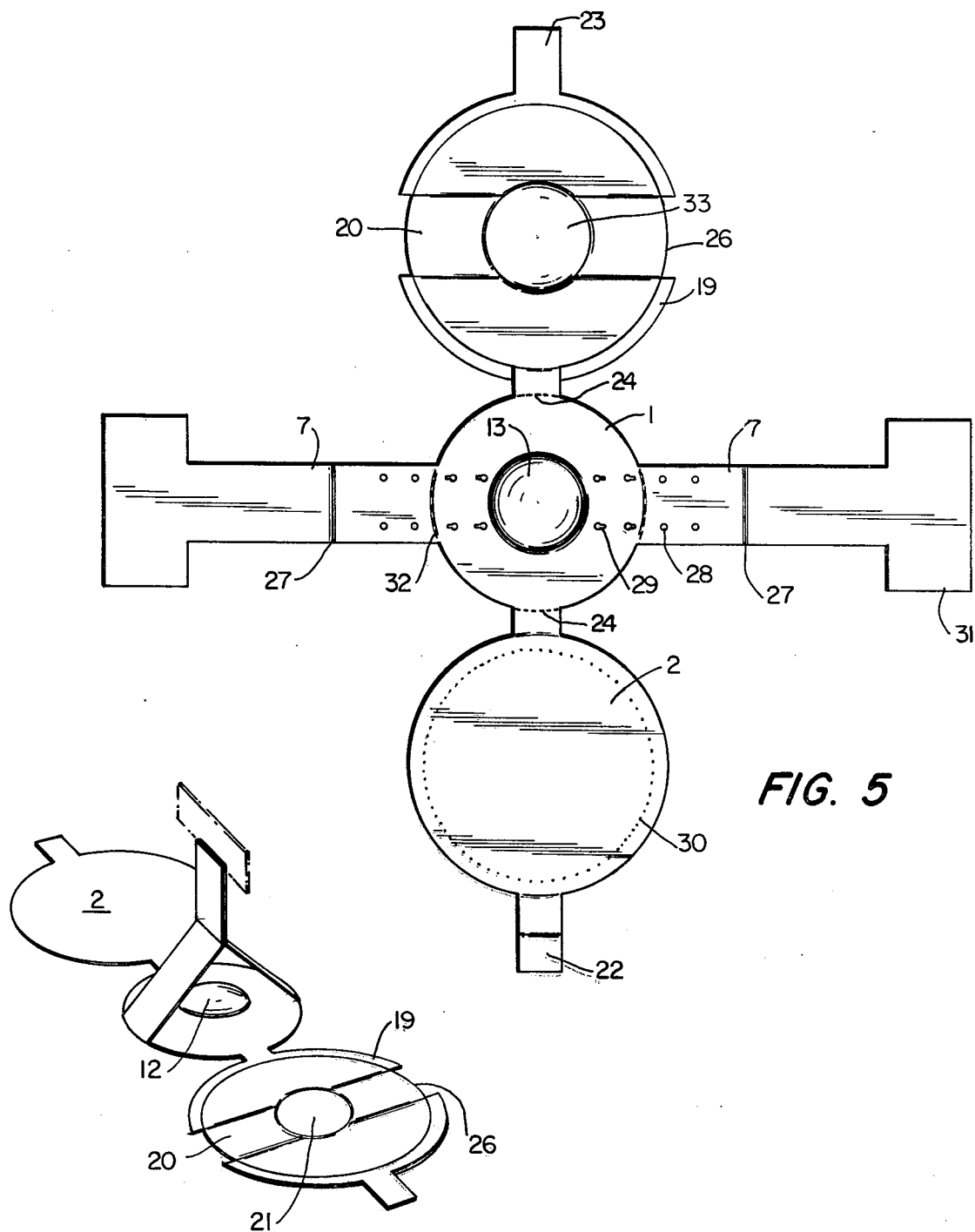
FIG. 5 is a top view of one embodiment of the present invention in which the bandage is fully opened and laid out flat. In the embodiment shown in FIG. 5, the applicator portion of the bandage is formed by two separate opposed sections which are separate from the top and bottom covers.
FIG. 6 is a perspective view of the bandage of FIG. 5 and shows the applicator tabs brought together over the central absorbent portion of the bandage.

FIG. 5 particularly illustrates an additional embodiment of the present invention and also the important feature whereby the present invention can be fabricated out of a single piece of material. In FIG. 5 the applicator portion of the bandage is provided by two opposing tabs 7 which are separate and distinct from the top protective cover 26. The centrally disposed backing of the bandage 1 is provided, as in the other illustrated embodiment of the invention, with a pad of absorbent material 13 which is disposed above the backing 1. The underside (not shown) of backing 1 is covered around the pad of absorbent material with adhesive material. The pad of absorbent material 13 is covered by a bubble or cap of deformable material 12 in the same manner as described in FIG. 2. This cap of deformable material is capable of being depressed to force the absorbent material 13 to extend and be maintained in a position below the lower surface of the backing 1 so that pressure can be maintained at the point of application. The tabs 7 are flexibly and removably attached to the backing 1 at 32. This attachment can conveniently be accomplished by providing a weakened and/or perforated area at the point of attachment. Flexing strips 27 are also provided transverse to the tabs 7 to permit flexing or creasing of the tabs as shown for example in FIG. 6 of the drawing. Thus, the terminal portions of the tabs 7 can be brought together in opposing relationship as shown in FIG. 6 to provide a convenient applicator for applying the bandage. Pressure is applied to the bubble 12 and absorbent material contained therein by simply pressing down on the applicator maintained in the configuration shown in FIG. 6. The portion 7 of the tabs proximate to the backing 1 are also provided with projecting nipples 28 which engages the slots 29 on the backing 1 when the applicator tabs are downwardly depressed, subsequent to application of the bandage and pressurizing of the absorbent pad and its compressible cap. A pinching inward motion of the applicator tabs 7 produces a slight inward motion of the nipples 28 through the slots 29 to assist in tearing the tabs away from the backing 1. This separation occurs at the weakened portion 32 of the bandage and permits separation of the applicator tabs by a simple, one handed motion, immediately after the bandage is in place.

Prior to use, the bandage illustrated in FIGS. 5 and 6 is folded into a compact, relatively flat, packet by bringing the ends of the applicators together as shown in FIG. 6 and folding the joined portion lightly downward over the cap 12 without actually compressing the cap. In this manner, the entire length of the applicators 7 can be folded within the confine of the backing 1. The top cover 26 which is provided with recesses 20 to accommodate the folded tabs and a similarly recessed cap 33 to accommodate the raised portion of the bandage caused by the uncompressed cap 12. The bottom cover 2 of the bandage folds under the backing 1 to provide a covering against the adhesive coated under-surface of the bandage. A tab 22 is conveniently provided on the bottom cover 2 and a tear portion 24 permits ultimate removal of the bottom cover 2 from the backing 1. A similar tab 23 facilitates tearing away of the top cover 26 from the backing 1 at 24. The top cover 26 is also provided at 19 with an overhanging portion to enclose the sides of the bandage. The top and bottom covers are suitably sealed together with adhesive or other means at 30. Although not specifically illustrated in FIGS. 5 and 6 additional portions 31 may be provided at either end of the applicators 7 to accommodate an enclosed swab of absorbent material which can be impregnated as described heretofore.

Figure 7:
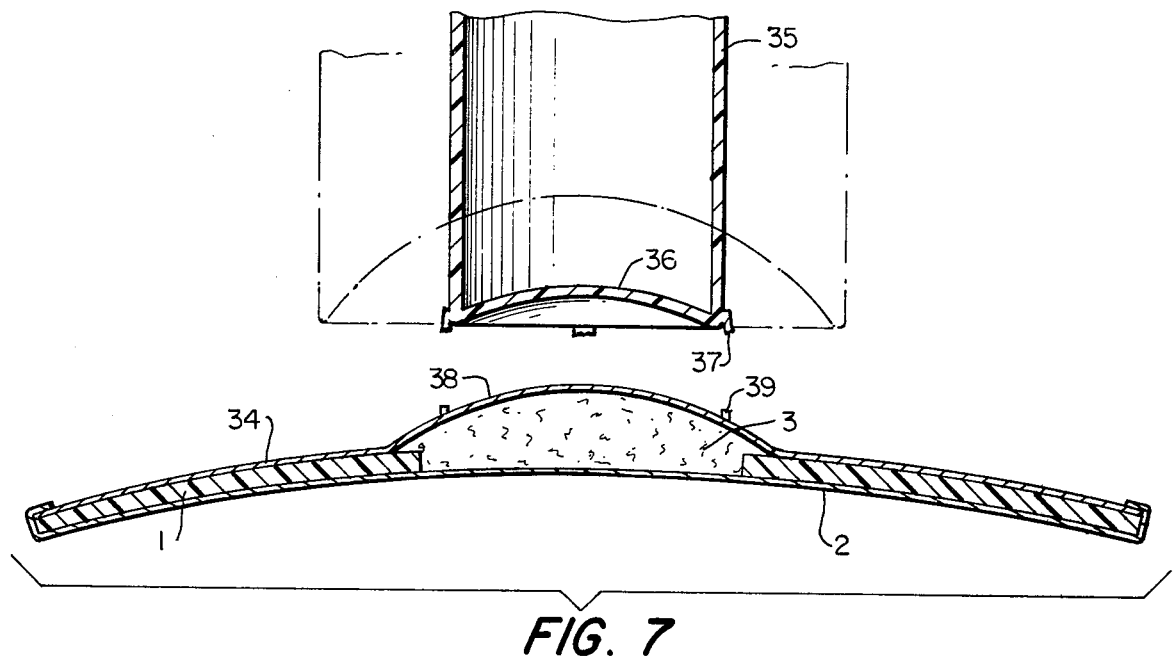
FIG. 7 is a side view of the bandage of the invention in which the applicator is a hollow tubular cylinder which is attached to a collapsible cap containing the absorbent pad.
Figure 8:
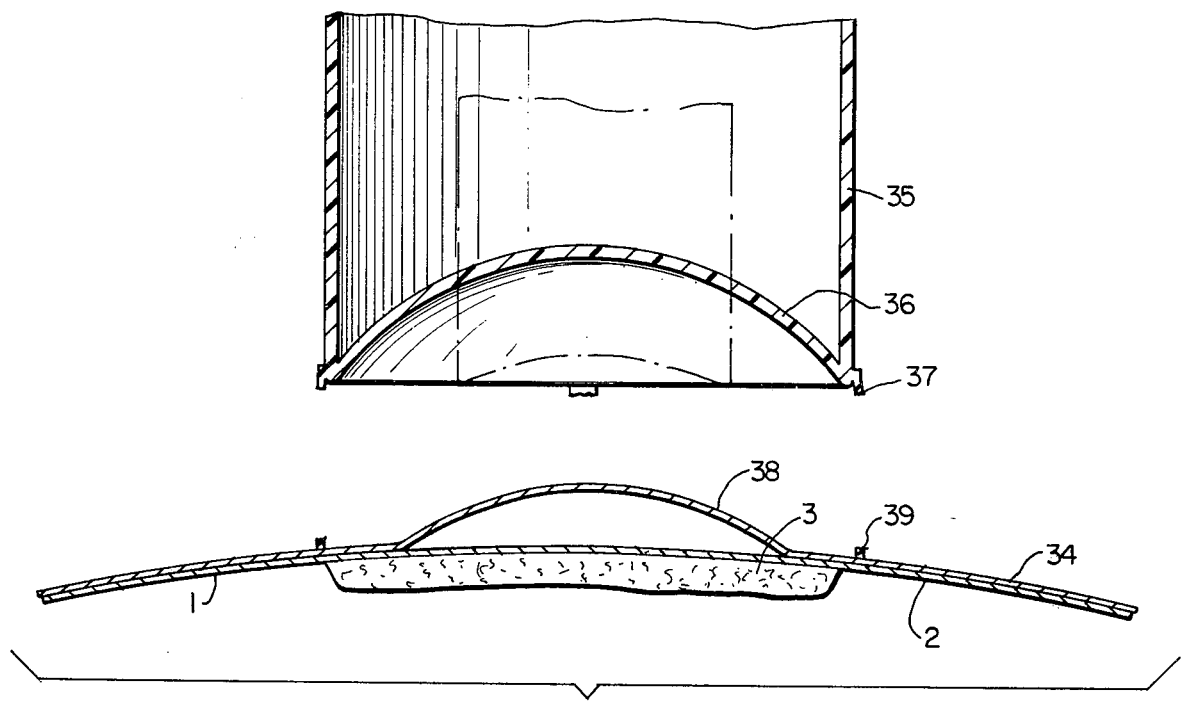
FIG. 8 is a side view of the bandage in which the tubular applicator is attached to the backing of the bandage and encloses the cap.

FIGS. 7 and 8 particularly illustrate the embodiment of the invention in which the applicator is a rigid, tubular member 35 disposed vertically on the backing 1 of the bandage. In FIG. 7 the tubular applicator 35 is of smaller diameter than the deformable cap 38 which encloses the absorbent pad 3 and is provided with a recessed end portion 36 which is contoured to the cap 38. In the embodiment shown the cap 38 extends on either side of the absorbent pad 3 to also cover a portion of the backing 1. Engagement of the applicator 35 with the cap 38 is conveniently provided by means of breakaway tabs 37 (39 being the portion of the tab attached to the cap).

Once the bandage is in place, the absorbent pad is displaced downward to form a bulge extending below the surface of the backing 1 by pressing down on the applicator 35 to collapse the cap 38. Lateral displacement of the pad 3 is inhibited by the edges of the backing 1 which extend beyond the perimeter of the cap to confine the pad. Once the bandage has been applied the applicator is easily removed by breaking away at the tabs 37–39.

In FIG. 8, a similar configuration to FIG. 7 is shown except that the absorbent pad 3 is conventionally disposed below the backing 1. The tubular applicator 35 is of larger diameter and directly attaches at 37–39 to the flat portion of the top cover 34 rather than the cap 38.

Figures 9, 10, 11:
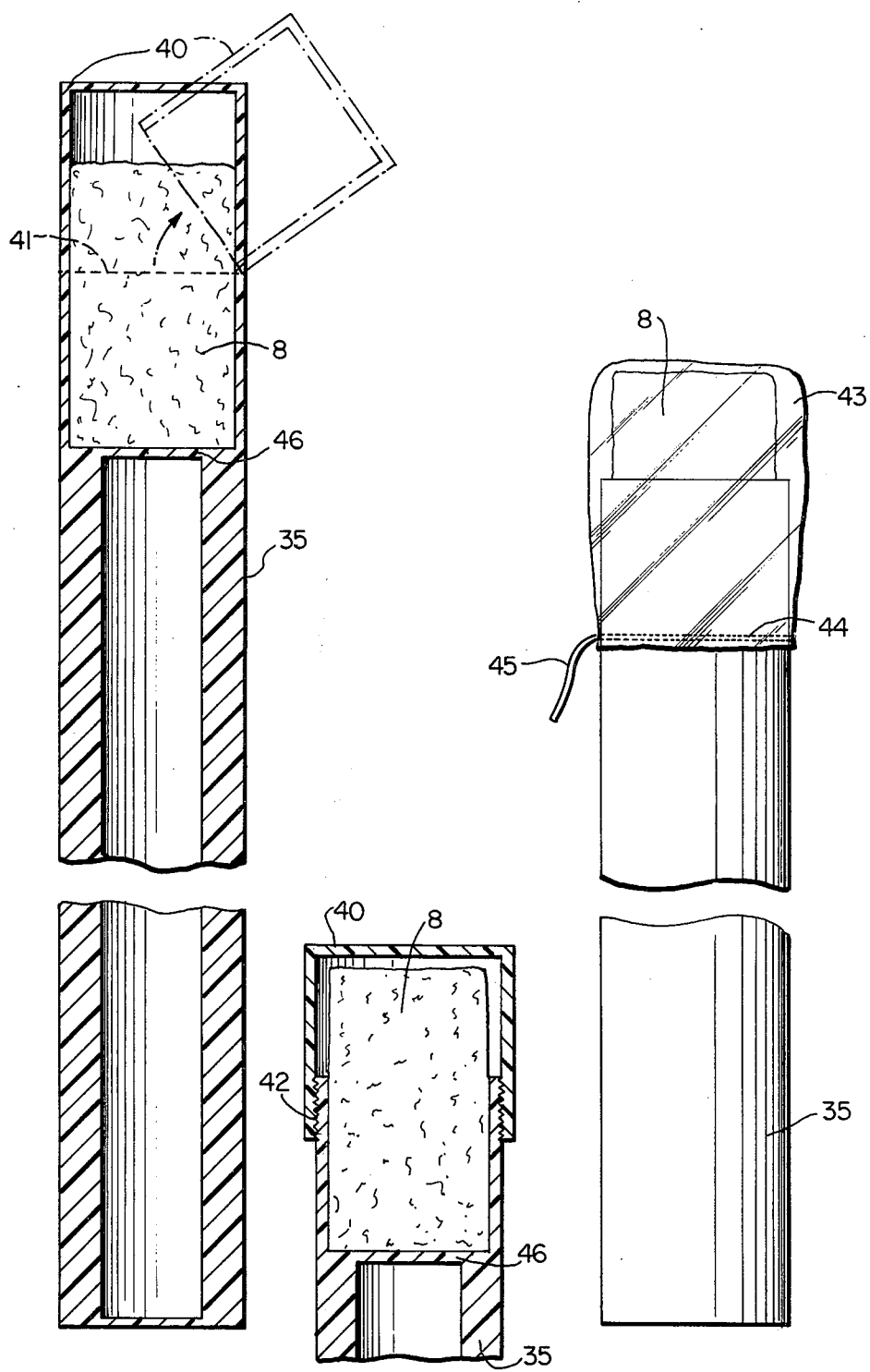
FIGS. 9, 10 and 11 show different embodiments of the absorbent swab attached at the end of the applicator remote from the attachment to the bandage.

FIGS. 9–11 illustrate various embodiments for enclosing swabs at the end of the applicator 35. In FIG. 9, the absorbent swab 8, which can be impregnated with a cleansing or medicinal preparation is enclosed in a portion of end of the applicator 35 by a partition 46. The upper portion 40 of the enclosure is a cap which can be broken off at 41 to expose the swab 8.

In FIG. 10, a similar arrangement to FIG. 9 is shown except that the cap 40 is attached to the applicator 35 by means of threads 42 and is removed by unscrewing the cap. FIG. 11 illustrates the swab 8 being simply enclosed by a bag 43. A tear portion 44 and tear string 45 are provided for removal of the protective bag to expose the swab 8.

The rigid, tubular applicator while not conveniently collapsible into a flat package, nevertheless has the advantage of permitting accurate efficient placement of the bandage with one hand and without coming into proximity with the sterile surface. While various materials can be used for the tubular applicator, a simple plastic tube such as commonly used to enclose syringes is satisfactory.

Generally the materials used in the bandage of the invention are conventional. The backing should have some degree of "stiffness" while remaining flexible enough to be contoured as required by the area of application. The applicator should be relatively firm, however, in order to transmit downward pressure during application.

While the features of the various embodiments of the present invention can be combined in a number of ways, a common feature is the vertically disposed applicator which facilitates efficient placement of the bandage with reduced risk of contact to the sterile absorbent pad of the bandage. It is also an important feature of the invention that an enclosed, pre-treated, swab can be attached to the end of the applicator.

I claim:

1. A unitary bandage comprising a flexible or semi-rigid backing having adhesive material applied to one side and an absorbent pad centrally disposed on said backing, applicator means for applying said bandage removably attached to said backing and disposed to extend vertically from the top surface thereof whereby to permit pressure to be applied downward against said backing, and bottom cover means removably attached to said backing for covering the adhesive side of the backing and the lower surface of said pad.

2. The bandage of claim 1 wherein said applicator is further disposed to cover the top of said absorbent pad thereby providing a protective cover for said pad.

3. The bandage of claim 2 wherein said applicator comprises a single strip of rigid or semi-rigid material flexibly and removably attached at one end to a side of said backing and adapted to lay substantially flat over said backing and pad to form a top protective cover for the backing and pad; said strip further being provided with a flexible portion which permits said strip to be upturned vertically to said backing.

4. The bandage of claim 2 wherein said applicator comprises a pair of rigid or semi-rigid strips each flexibly and removably attached at an opposing edge of said backing and centrally joined over said pad to form a single, upward projecting strip.

5. The bandage of claim 2 wherein said applicator is a rigid hollow tube having a diameter generally the same as said pad and disposed vertical to said backing to extend upward and enclose said pad.

6. The bandage of claim 2 wherein the unattached end of said applicator has attached thereto a swab of absorbent material.

7. The bandage of claim 4 wherein top cover means for enclosing the top of said bandage is flexibly and removably attached to an edge of said backing opposite the side to which said bottom cover means is attached.

8. The bandage of claim 2 which includes means disposed on the non-adhesive side of said backing for downwardly displacing said pad to a position partially extending below the backing.

9. The bandage of claim 8 wherein said applicator is a rigid tube having about the diameter of said pad and disposed vertical to said backing and in a position to displace by downward pressure said pad displacing means.

10. The bandage of claim 6 wherein said swab is impregnated with antiseptic or cleansing material and sealed in an air tight container.

11. The bandage of claim 1 wherein said bottom cover is disposed on said backing to permit removal from the side.

12. The bandage of claim 8 wherein said means for downwardly displacing said pad is a collapsible cap means for also maintaining said pad in its displaced position.

13. The bandage of claim 12 wherein said applicator is disposed over said cap means to permit downward pressure to be applied to said cap means.

14. The bandage of claim 7 wherein said backing and applicator are formed from a single sheet of material.

* * * * *